(12) United States Patent
Slager et al.

(10) Patent No.: US 11,298,451 B2
(45) Date of Patent: Apr. 12, 2022

(54) HEMODIALYSIS CATHETER SLEEVE

(71) Applicant: Surmodics, Inc., Eden Prairie, MN (US)

(72) Inventors: Joram Slager, St. Louis Park, MN (US); Joe McGonigle, Minneapolis, MN (US); Anh Tri La, Minneapolis, MN (US); David E. Babcock, Brooklyn Park, MN (US); Bruce Jelle, Minnetonka, MN (US); Aleksey Kurdyumov, Lino Lakes, MN (US); Timothy M. Kloke, Victoria, MN (US); Charlie Olson, Eden Prairie, MN (US); Gary Maharaj, Eden Prairie, MN (US); Nathan Lockwood, Minneapolis, MN (US)

(73) Assignee: Surmodics, Inc., Eden Prairie, MN (US)

(*) Notice: Subject to any disclaimer, the term of this patent is extended or adjusted under 35 U.S.C. 154(b) by 116 days.

(21) Appl. No.: 16/685,642

(22) Filed: Nov. 15, 2019

(65) Prior Publication Data
US 2020/0188573 A1 Jun. 18, 2020

Related U.S. Application Data

(63) Continuation of application No. 15/257,252, filed on Sep. 6, 2016, now Pat. No. 10,478,546.
(Continued)

(51) Int. Cl.
*A61M 1/36* (2006.01)
*A61M 25/10* (2013.01)
(Continued)

(52) U.S. Cl.
CPC ....... *A61M 1/3661* (2014.02); *A61B 17/3415* (2013.01); *A61M 1/3659* (2014.02);
(Continued)

(58) Field of Classification Search
CPC . A61B 17/3415; A61B 17/34; A61B 17/3498; A61B 2017/348;
(Continued)

(56) References Cited

U.S. PATENT DOCUMENTS 4,195,637 A 4/1980 Gruntzig et al.
4,973,993 A 11/1990 Allen
(Continued)

FOREIGN PATENT DOCUMENTS

CN 1056430 11/1991
CN 1929888 3/2007
(Continued)

OTHER PUBLICATIONS

File History for U.S. Appl. No. 15/257,252 downloaded Jan. 20, 2020 (316 pages).
(Continued)

*Primary Examiner* — Jason E Flick
(74) *Attorney, Agent, or Firm* — Pauly, DeVries Smith & Deffner LLC

(57) ABSTRACT

A hemodialysis vascular access device includes a proximal end sized and shaped to sealably couple to a hemodialysis catheter, a movable structure coupled to the proximal end, a fixation structure coupled to the movable region and sized and shaped for fixation on a patient, an elongated sleeve coupled to the fixation structure and sized and shaped for insertion into a patient's vasculature, and a valve at a distal end of the internal lumen. When a hemodialysis catheter is inserted into the device and coupled to the proximal end, distal movement of the proximal end relative to the fixation
(Continued)

structure biases a distal end of the hemodialysis catheter from a position inside the elongated sleeve through a valve out of the device and into the patient's blood.

19 Claims, 11 Drawing Sheets

Related U.S. Application Data

(60) Provisional application No. 62/218,849, filed on Sep. 15, 2015.

(51) Int. Cl.
*A61M 39/02* (2006.01)
*A61B 17/34* (2006.01)
*A61M 25/00* (2006.01)
*A61M 25/06* (2006.01)

(52) U.S. Cl.
CPC .... *A61M 25/0017* (2013.01); *A61M 25/0097* (2013.01); *A61M 25/10* (2013.01); *A61M 39/0247* (2013.01); *A61M 2025/0681* (2013.01); *A61M 2039/027* (2013.01); *A61M 2039/0258* (2013.01); *A61M 2039/0273* (2013.01); *A61M 2205/0238* (2013.01); *A61M 2210/125* (2013.01)

(58) Field of Classification Search
CPC ........ A61B 2017/3492; A61M 1/3659; A61M 1/3661; A61M 1/36; A61M 1/3621; A61M 1/3653; A61M 2025/0681; A61M 2039/0258; A61M 2039/027; A61M 2039/0273; A61M 2205/0238; A61M 2210/125; A61M 25/0017; A61M 25/0097; A61M 25/10; A61M 39/0247; A61M 25/01; A61M 25/06; A61M 25/0662; A61M 39/00; A61M 39/02
See application file for complete search history.

(56) References Cited

U.S. PATENT DOCUMENTS

| | | | |
|---|---|---|---|
| 5,041,089 A | 8/1991 | Mueller et al. | |
| 5,087,246 A | 2/1992 | Smith | |
| 5,254,107 A | 10/1993 | Soltesz | |
| 5,318,587 A | 6/1994 | Davey | |
| 5,382,234 A | 1/1995 | Cornelius et al. | |
| 5,414,075 A | 5/1995 | Swan et al. | |
| 5,556,308 A | 9/1996 | Brown et al. | |
| 5,571,089 A | 11/1996 | Crocker | |
| 5,582,165 A * | 12/1996 | Bryan ............... | A61M 39/284 128/207.14 |
| 5,637,460 A | 6/1997 | Swan et al. | |
| 5,714,360 A | 2/1998 | Swan et al. | |
| 5,776,101 A | 7/1998 | Goy | |
| 5,807,331 A | 9/1998 | Den Heijer et al. | |
| 5,858,653 A | 1/1999 | Duran et al. | |
| 5,876,374 A | 3/1999 | Alba et al. | |
| 5,882,336 A | 3/1999 | Janacek | |
| 6,007,833 A | 12/1999 | Chudzik et al. | |
| 6,077,698 A | 6/2000 | Swan et al. | |
| 6,156,016 A | 12/2000 | Maginot | |
| 6,190,371 B1 | 2/2001 | Maginot et al. | |
| 6,278,018 B1 | 8/2001 | Swan | |
| 6,394,995 B1 | 5/2002 | Solar et al. | |
| 6,465,178 B2 | 10/2002 | Chappa et al. | |
| 6,491,680 B1 | 12/2002 | Batiste | |
| 6,514,734 B1 | 2/2003 | Clapper et al. | |
| 6,517,515 B1 | 2/2003 | Eidenschink | |
| 6,537,254 B1 * | 3/2003 | Schock ............... | A61M 25/0111 604/167.03 |
| 6,603,040 B1 | 8/2003 | Swan | |
| 6,623,504 B2 | 9/2003 | Vrba et al. | |
| 6,762,019 B2 | 7/2004 | Swan et al. | |
| 6,896,842 B1 | 5/2005 | Hamilton et al. | |
| 7,138,541 B2 | 11/2006 | Swan | |
| 7,163,523 B2 | 1/2007 | Devens, Jr. et al. | |
| 7,309,593 B2 | 12/2007 | Ofstead et al. | |
| 7,348,055 B2 | 3/2008 | Chappa et al. | |
| 7,736,689 B2 | 6/2010 | Chappa et al. | |
| 7,772,393 B2 | 8/2010 | Guire et al. | |
| 7,807,750 B2 | 10/2010 | Taton et al. | |
| 8,039,524 B2 | 10/2011 | Chappa et al. | |
| 8,487,137 B2 | 7/2013 | Guire et al. | |
| 8,513,320 B2 | 8/2013 | Rooijmans | |
| 8,679,063 B2 * | 3/2014 | Stout ............... | A61M 25/0045 604/164.01 |
| 8,809,411 B2 | 8/2014 | Rooijmans | |
| 8,889,760 B2 | 11/2014 | Kurdyumov et al. | |
| 10,478,546 B2 | 11/2019 | Slager et al. | |
| 10,918,835 B2 | 2/2021 | Murphy | |
| 2005/0059925 A1 * | 3/2005 | Maginot ............ | A61M 25/0194 604/43 |
| 2007/0032882 A1 | 2/2007 | Lodhi et al. | |
| 2008/0125750 A1 * | 5/2008 | Gaissert ............ | A61M 25/0017 604/523 |
| 2010/0198168 A1 | 8/2010 | Rooijmans | |
| 2010/0228333 A1 | 9/2010 | Drasler et al. | |
| 2010/0274012 A1 | 10/2010 | Guire et al. | |
| 2011/0106014 A1 * | 5/2011 | Helm, Jr. ............ | A61M 25/02 604/178 |
| 2011/0144373 A1 | 6/2011 | Swan et al. | |
| 2012/0148852 A1 | 6/2012 | Jelle et al. | |
| 2012/0149934 A1 | 6/2012 | Kurdyumov | |
| 2012/0221024 A1 | 8/2012 | Sutton et al. | |
| 2012/0274012 A1 | 11/2012 | Guenther et al. | |
| 2012/0296313 A1 | 11/2012 | Andreacchi et al. | |
| 2013/0143056 A1 | 6/2013 | Swan et al. | |
| 2013/0237950 A1 | 9/2013 | Gianotti et al. | |
| 2013/0302529 A1 | 11/2013 | Kurdyumov | |
| 2014/0025044 A1 | 1/2014 | Zamarripa et al. | |
| 2015/0190618 A1 | 7/2015 | Kantor | |
| 2017/0072129 A1 | 3/2017 | Slager et al. | |
| 2017/0281913 A1 | 10/2017 | Murphy | |

FOREIGN PATENT DOCUMENTS

| | | |
|---|---|---|
| CN | 101048188 | 10/2007 |
| CN | 101056667 | 10/2007 |
| CN | 101219242 | 7/2008 |
| CN | 201683986 | 12/2010 |
| CN | 102006902 | 4/2011 |
| CN | 102223993 | 11/2011 |
| CN | 102553057 | 7/2012 |
| CN | 103476450 | 12/2013 |
| CN | 108348728 | 7/2018 |
| EP | 3349834 | 7/2018 |
| EP | 3436095 | 2/2019 |
| EP | 3349834 | 1/2021 |
| WO | 2008039910 | 4/2008 |
| WO | 2014186729 | 11/2014 |
| WO | 2015077545 | 5/2015 |
| WO | 2017048576 | 3/2017 |
| WO | 2017172607 | 10/2017 |

OTHER PUBLICATIONS

File History for U.S. Appl. No. 15/467,350 downloaded Jan. 20, 2020 (183 pages).
File History for European Patent Application No. 16770135.8 downloaded Jan. 20, 2020 (233 pages).
"International Preliminary Report on Patentabililty," for PCT Application No. PCT/US2017/024286 dated Oct. 11, 2018 (12 pages).
"International Preliminary Reporton Patentability," for PCT Application No. PCT/US2016/050703 dated Mar. 29, 2018 (9 pages).
"International Search Report and Written Opinion," for PCT application No. PCT/US2016/050703 dated Dec. 16, 2016 (14 pages).

(56) References Cited

OTHER PUBLICATIONS

"International Search Report and Written Opinion," for PCT Application No. PCT/US2017/024286 dated Jul. 5, 2017 (19 pages).
Love, Kevin T. et al., "Lipid-Like Materials for Low-Dose In Vivo Gene Silencing," PNAS Feb. 2010, 107 (5) 1864-1869, www.pnas.org/cgi/doi/10.1073/pnas.0910603106 (6 pages).
"Final Office Action," for U.S. Appl. No. 15/467,530 dated Mar. 18, 2020 (22 pages).
"First Office Action," for Chinese Patent Application No. 2016800647381 dated Mar. 25, 2020 (27 pages) with English Translation.
"Non-Final Office Action," for U.S. Appl. No. 15/467,530 dated Jun. 29, 2020 (14 pages).
"Notice of Allowance," for U.S. Appl. No. 15/467,530 dated Oct. 13, 2020 (13 pages).
"Response to Final Office Action," for U.S. Appl. No. 15/467,530, filed Jun. 17, 2020 (11 pages).
"Response to Non-Final Office Action," for U.S. Appl. No. 15/467,530, filed Sep. 29, 2020 (7 pages).
"Second Office Action," for Chinese Patent Application No. 2016800647381 dated Sep. 16, 2020 (23 pages) with English Translation.
"Third Office Action," for Chinese Patent Application No. 2016800547381 dated Jan. 21, 2021 (17 pages) with English Translation.

\* cited by examiner

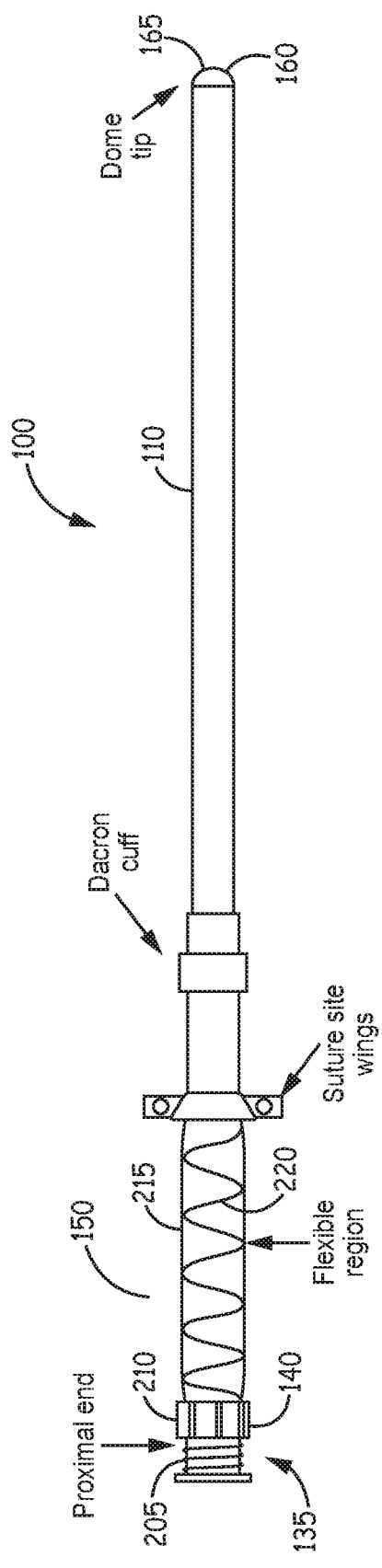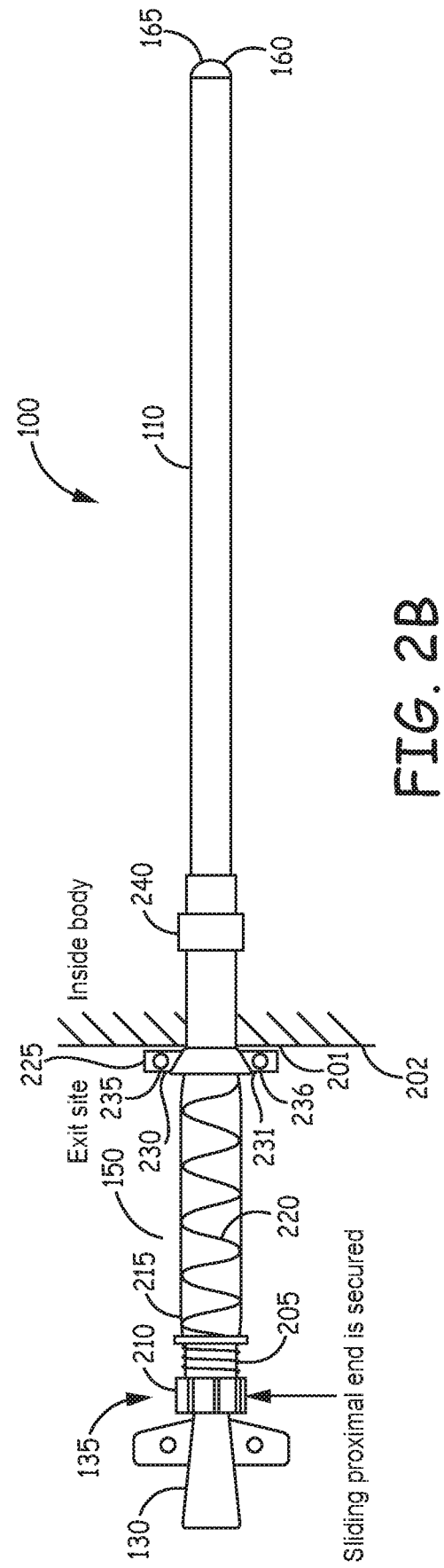
FIG. 2A
FIG. 2B

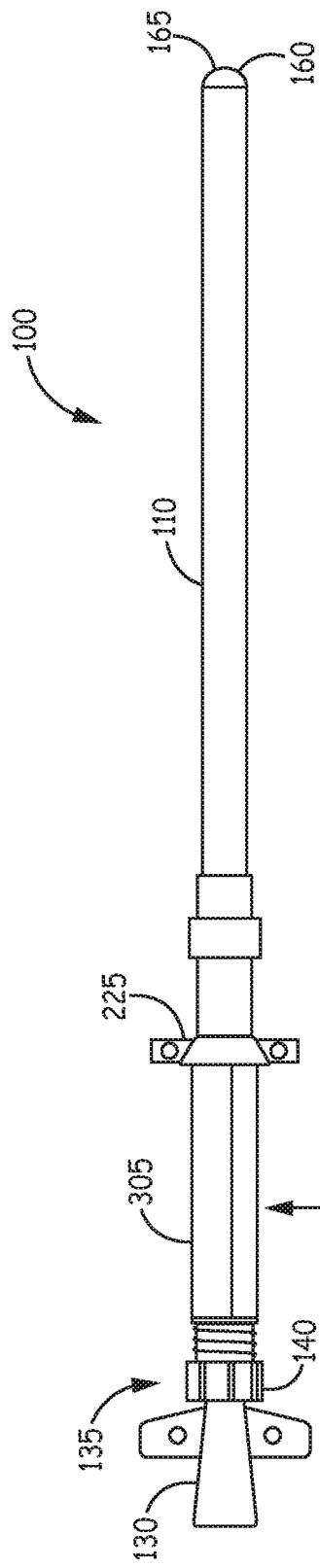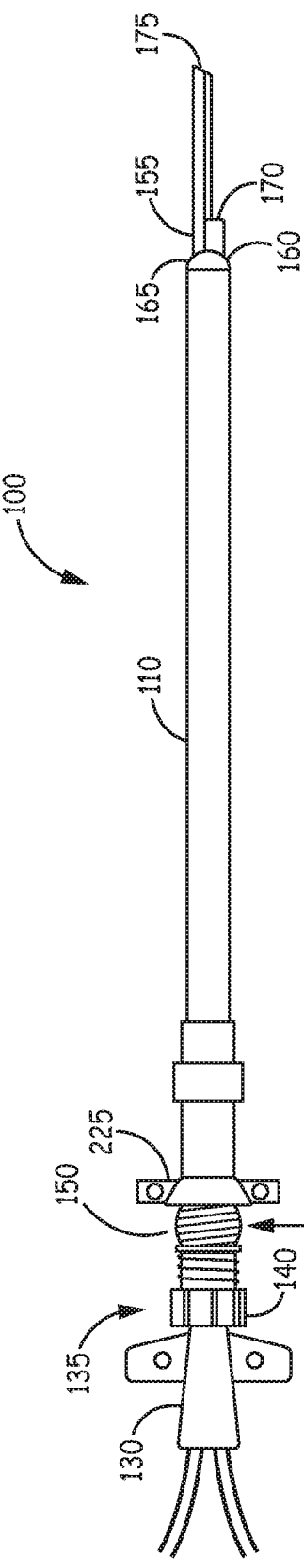
FIG. 3A
FIG. 3B
Protective cover for flexible region
Flexible region is compressed

HEMODIALYSIS CATHETER SLEEVE

This application is a continuation of U.S. patent application Ser. No. 15/257,252, filed Sep. 6, 2016, which claims the benefit of U.S. Provisional Application No. 62/218,849, filed Sep. 15, 2015, the contents of which are herein incorporated by reference.

TECHNICAL FIELD

This document relates generally to medical device access systems, and more particularly, to systems, devices and methods for long-term access to a body vessel.

BACKGROUND

Hemodialysis is available for patients who have health issues, such as kidney failure. In a hemodialysis procedure, blood is drawn from a patient, filtered to remove substances such as salts or wastes, and then returned to the patient. A kidney failure patient may be required to follow a hemodialysis treatment protocol for months or years. Some patients receive treatment using a hemodialysis catheter that is inserted into the vasculature and periodically used according to a treatment regimen.

Indwelling catheters such as hemodialysis catheters are sometimes employed for long-term access to internal areas of a patient, such as several weeks or even several months. For example, a hemodialysis catheter may be left in place for three to six months or longer while an arteriovenous (AV) graft or arteriovenous fistula matures. When a catheter is left in place long term, i.e. for weeks or months, problems may arise with the patency of the catheter. For example, hemodialysis catheters are prone to occlusion from fibrin sheath and thrombus formation. When this happens, complex interventional treatments can be required, ranging from flushing of the lumen with thrombolytic agents to fibrin sheath stripping or catheter removal and reinsertion of another catheter. These treatments can be invasive or undesirable for the patient, and expensive for the health care system. There is therefore a need to maintain patency of hemodialysis catheters to reduce the complex interventional treatments.

SUMMARY

An example vascular access device includes an elongated body insertable into a vessel and including a distal lumen extending to a distal orifice, a proximal portion including a proximal orifice and a proximal lumen in communication with the distal lumen, the proximal lumen defining an axis. The proximal lumen and distal lumen configured to receive a catheter through the proximal orifice and extending through the proximal lumen and distal lumen. The proximal orifice is axially displaceable toward the elongated body from a first position to a second position. When a distal end of the catheter is situated inside the distal lumen of the elongated body, the proximal orifice is in the first location. When the distal end of the catheter extends beyond the distal orifice the proximal orifice is in the second position.

An example hemodialysis device includes a dialysis catheter having a proximal end, an elongated body, and a distal end; a sleeve sized and shaped to receive the dialysis catheter, the sleeve having a valve proximate to a distal orifice, and a compressible section coupled to a proximal end of the sleeve, the compressible section also coupled to the dialysis catheter at a location proximal to the proximal end of the sleeve. Distal movement of the proximal end of the compressible section moves the dialysis catheter distally within the sleeve from a first configuration in which distal end of the catheter resides inside the sleeve to a second configuration in which the catheter extends through the valve and out a distal end of the sleeve.

An example hemodialysis vascular access device includes a proximal end sized and shaped to sealably couple to a hemodialysis catheter, a movable structure coupled to the proximal end, a fixation structure coupled to a non-movable region and sized and shaped for fixation on a patient, an elongated sleeve coupled to the fixation structure and sized and shaped for insertion into a patient's vasculature, and a valve at a distal end of the internal lumen. When a hemodialysis catheter is inserted into the device and coupled to the proximal end, distal movement of the proximal end relative to the fixation structure biases a distal end of the hemodialysis catheter from a position inside the elongated sleeve through a valve out of the device and into the patient's blood.

An example method of using a dialysis catheter includes inserting a sleeve into the vasculature of a patient, inserting a catheter into the sleeve, a distal end of the catheter residing in the sleeve, coupling a proximal end of the catheter to a compressible section that can be coupled to the sleeve and moving the catheter distally to extend a distal end of the catheter out of a distal end of the sleeve and into the patient's vasculature. In some examples, a method includes first inserting the catheter into the sleeve, with the distal end of the catheter protruding past the distal end of the sleeve, then inserting this catheter/sleeve assembly into the vasculature of the patient.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various examples are illustrated by way of example in the figures of the accompanying drawings. Such examples are demonstrative and not intended to be exhaustive or exclusive examples of the present subject matter.

FIG. 2A illustrates, by way of example, an embodiment of a hemodialysis vascular access device.

FIG. 2B illustrates, by way of example, an embodiment of a hemodialysis vascular access device with a catheter inserted into the access device.

FIG. 3A illustrates, by way of example, an embodiment of a hemodialysis vascular access device with a catheter inserted into the device and a protective cover over a compressible region.

FIG. 3B illustrates, by way of example, an embodiment of a hemodialysis vascular access device with a catheter inserted into the access device and advanced to protrude from a valve at a distal end of the access device.

DETAILED DESCRIPTION

Figure 1:
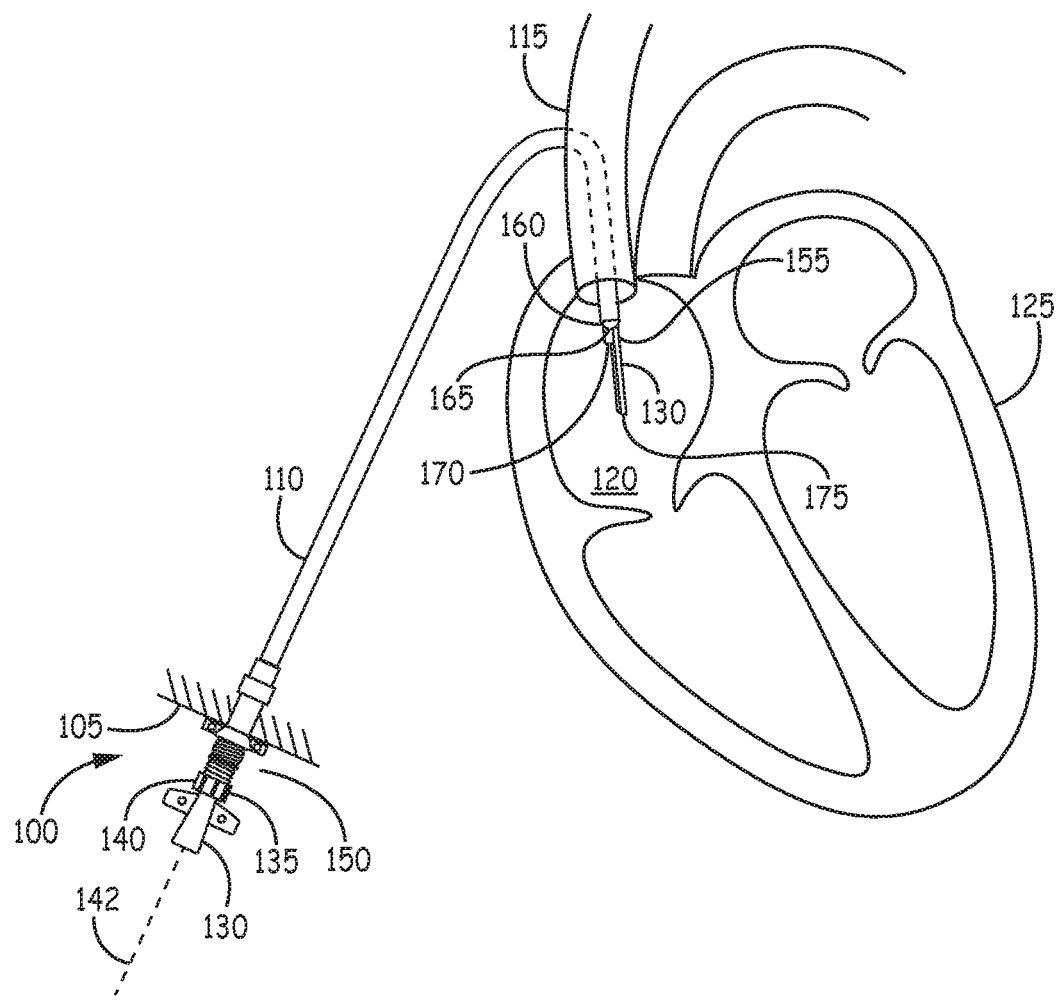
FIG. 1 illustrates an example hemodialysis access device with a hemodialysis catheter inserted into the device and extending out of the device an into the bloodstream.

The following detailed description of the present subject matter refers to the accompanying drawings which show, by way of illustration, specific aspects and examples in which the present subject matter may be practiced. These examples are described in sufficient detail to enable those skilled in the art to practice the present subject matter. Other examples may be utilized and structural, logical, and electrical changes may be made without departing from the scope of the present subject matter. References to "an", "one", or "various" examples in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

An example hemodialysis vascular access device includes a sleeve that receives a hemodialysis catheter. The access device can be attached to the body, for example using sutures. A portion of the access device that remains on the outside of the patient's body includes a proximal opening that can receive a catheter. The access device also includes an elongated sleeve body that extends into the vasculature of a patient. At the distal end of the sleeve body, a valve prevents blood from entering the sleeve. When hemodialysis is not being performed, the catheter resides within the sleeve, and the valve at the distal end of the sleeve body can be closed. The catheter may be mounted to a structure, such as a cap, at or near the proximal end of the access device. To use the catheter for hemodialysis, the catheter can be pushed further into the device, so that the distal end of the catheter pushes past the valve and into the patient's blood. To accommodate this movement, a proximal portion of the access device moves distally as the catheter is inserted. In an example, a proximal portion of the catheter compresses to allow this axial movement. In various examples, gaseous fluid (such as air) can be allowed to exit the device through a permeable membrane or valve, or displaced to a low pressure zone such as a balloon or bladder. This avoids injection of gaseous fluid into the sleeve. When a hemodialysis procedure is complete, the catheter can be typically flushed with a solution, such as heparin, to help keep the catheter unobstructed. Because the catheter is usually housed within the sleeve during the time between hemodialysis procedures, the catheter is less prone to occlusion or blockage from fibrin sheath growth or thrombus formation. In some embodiments of the vascular device described herein, the catheter can effectively be flushed with solutions of antiplatelet to reduce fibrin or antimicrobial or antibacterial agents to reduce infection because the catheter is housed and protected within the sleeve. For these embodiments a port can be provided on the vascular access device to aid in flushing the space between the sleeve and the catheter.

In an example, a catheter has a captured axial length from a distal tip to a proximal fixation point. The captured axial length is captured within a portions of a vascular access device, such as within a sleeve and compressible section. The catheter can be securable at or near a proximal orifice of the vascular access device. The vascular access device can have a variable lumen length from the proximate orifice to a distal orifice. In an expanded state, the variable lumen length is longer than the captured axial length of the catheter. In a contracted state, the variable lumen length of the vascular access device can be shorter than the captured axial length of the catheter. In an example, a proximal orifice is moveable from a first position, at which the access device is in an expanded state, to a second position, at which the access device is in a contracted state. By moving the proximal orifice, and thus a catheter that is coupled to the proximal orifice, the distal end of the catheter can be selectively extended from or retracted into the distal lumen of the access device. This selective movement can be used, for example, to extend the distal end of the catheter into and out of blood in a patient to allow, for example, access to blood during a hemodialysis procedure, but shield the catheter from blood when a procedure is not underway.

Referring now to examples shown in the figures, FIG. 1 illustrates an example hemodialysis access device 100 with a hemodialysis catheter 130 inserted into the device and extending out of a distal end 160 of the device an into the patient's blood. FIGS. 2A, 2B, 3A, and 3B show various features and configurations of the example embodiment illustrated in FIG. 1

Referring again to FIG. 1, a hemodialysis access device 100 is inserted through an incision site 105 in a patient's body. The access device 100 has a sleeve 110 that extends into the patient's vasculature 115 and optionally into the right atria 120 of the heart 125. A hemodialysis catheter 130 is inserted inside the access device 100 and through the sleeve 110. The sleeve inner diameter may, for example, be 15.5 French or smaller, but can be large enough to accommodate a hemodialysis catheter. A proximal end of the catheter may be coupled to a movable portion 140 of the access device 100, typically at or near the proximal end 135 of the access device 100. The movable portion 140 may, for example, be coupled to a compressible region 150 on the access device 100, so that the overall axial length of the access device 100 may be reduced by compressing the compressible region. When the movable portion 140 of the access device 100 is displaced distally along the axis 142 of the access device, a distal end 155 of the hemodialysis catheter 130 extends out of the distal end 160 of the sleeve 110.

The sleeve 110 may include a valve 165 that prevents blood from entering the distal end 160 of the sleeve 110 when the catheter is retracted into the sleeve, and permits the catheter to push through the valve 165 to enter the blood stream. The valve 165 may be designed to partially or fully seal around the catheter 130 to prevent entry of blood into the catheter when the catheter is extended through the valve and into the bloodstream. During a dialysis procedure, blood is drawn in through a first orifice 170 in the distal end 155 of the catheter and through a lumen (not shown) in the catheter, and processed outside the body to, for example, filter out waste or salt. The processed blood is then returned to the body through a second lumen (not shown) in the hemodialysis catheter and reintroduced into the blood stream through a second orifice 175 in the catheter.

When the sleeve remains in the vasculature of a body for a period of time, the sleeve 110 can become covered with a fibrin sheath. In this case, in some examples, when the hemodialysis catheter 130 is displaced out from the distal end 160 of the sleeve 110, the hemodialysis catheter 130 can break through the fibrin sheath and allow blood exchange. In some examples, the valve is designed to facilitate breaking of fibrin sheath that has accumulated at the distal end of the sleeve by pushing the catheter through the valve.

Figure 5A:
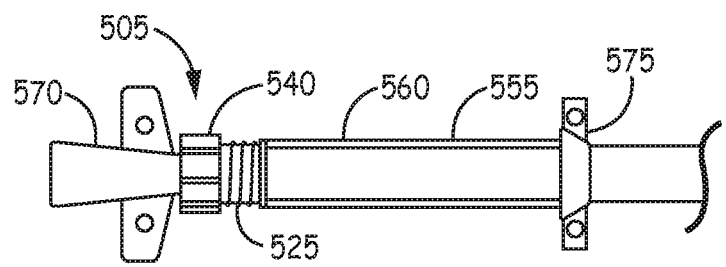
FIGS. 5A and 5B, are illustrations of a portion an example access device with a compressible section formed from a balloon.

Referring now to FIGS. 2A and 2B, an example access device 100 may include a threaded region 205 on the proximal end 135 of the device. A cap 210 with internal threads may be advanced onto the threaded region 205 to compress an internal seal onto a hemodialysis catheter 130. An example seal is shown in FIG. 5A. The cap 210 may form part of the movable portion 140 of the access device that translates axially to allow for displacement of the catheter 130 relative to the devices.

Various techniques may be used to allow the movable portion 140 and catheter to move relative to fixed portions of the access device. For example, portions of the access device may slide, pivot, translate, compress, or otherwise move relative to each other to accommodate axial displacement. For the purpose of illustration, a compressible region 150 is shown in FIGS. 2A and 2B. In an example, the compressible region 150 may be formed of a flexible material 215 that permits axial displacement of the movable portion 140 of the access device 100, so that the catheter can be advanced into the device. In an example, the flexible material 215 can be an air-permeable membrane that permits air movement out of the device during compression, to avoid driving air into the sleeve 110 and potentially into the body. Similarly, the membrane permits air movement into the catheter during retraction, to avoid creating a vacuum during retraction, which if translated to the sleeve may cause blood to draw into the distal end of the sleeve. The membrane may prohibit particles from entering the device, and may be an antimicrobial membrane. In an example, the membrane can be formed from a polypropylene material. In some examples, the membrane can be a non-woven material, such as non-woven polypropylene. The membrane may also be formed of polyethylene terephthalate, nylon, cotton, polyamide or polyester. An optional spring 220 may provide structural support. The spring can be made of metal such as stainless steel or nitinol. In some examples, the compressible region 150 includes an extendible pleated material. For example, the compressible region may be formed of an accordion-type pleated material that can be extended or compressed without stretching the material. In some examples, the compressible region can be formed of a plurality of layers of pleated material.

In some examples, one or more valves are provided on the device as an alternative or in addition to the permeable membrane. In an example, the one or more valves permit movement of a fluid such as air into the device when the catheter is pushed into the device. In various examples, the one or more valves permit fluid movement in and out of the device, or between regions of the device. In some examples, other structures such as a bladder or balloon are used in addition to a valve or membrane or both, or as an alternative to a valve or membrane. In an example, to accommodate movement of the movable portion 140, a balloon inflates and deflates as the movable portion 140 and catheter 130 are cycled with respect to the device.

FIG. 2B shows an example access device 100 inserted through a suture site 201 in a patient's body 202. The access device 100 may have a fixation structure 225 such as wings 230, 231 that allow for fixation of the access device in the incision. Sutures may be attached to the wings using holes 235, 236 in the wings. Inside the patient's body, a cuff 240 may be provided to further support fixation by ingrowth of tissue into the cuff over time. The cuff may, for example, be made of Polyethylene terephthalate, which is commercially available as Dacron®. In some exemplary embodiments the cuff could be impregnated or coated with antibacterial components. Exemplary antibacterial components include, but are not limited to, various silver-containing materials, antibiotics (e.g. rifampin/minocycline) or other antibacterial surface treatments (e.g. coating with quaternary ammonium containing polymers). In yet other embodiments, the sleeve could contain antibacterial components. Nano structured surfaces may also be employed to enhance surface antibacterial activity.

FIG. 3A illustrates, by way of example, an embodiment of a hemodialysis vascular access device with a catheter inserted into the device and a protective cover 305 over the compressible region 150.

FIG. 3B illustrates, by way of example, an embodiment of a hemodialysis vascular access device with a hemodialysis catheter 130 inserted into the access device 100 and advanced to protrude from a valve 165 at a distal end of the access device. The compressible region 150 is shown in a compressed configuration, which brings the movable portion 140 closer to the fixation structure 225 and moves the catheter 130 further into the device 100. The distal end 155 of the catheter 130 extends through the valve 165 and past the distal end 160 of the sleeve 110. On the proximal side of the catheter, protective cover 305 extends over the compressible region 150. The protective cover can be removed, i.e. when the compressible region is compressed.

Figure 4A:
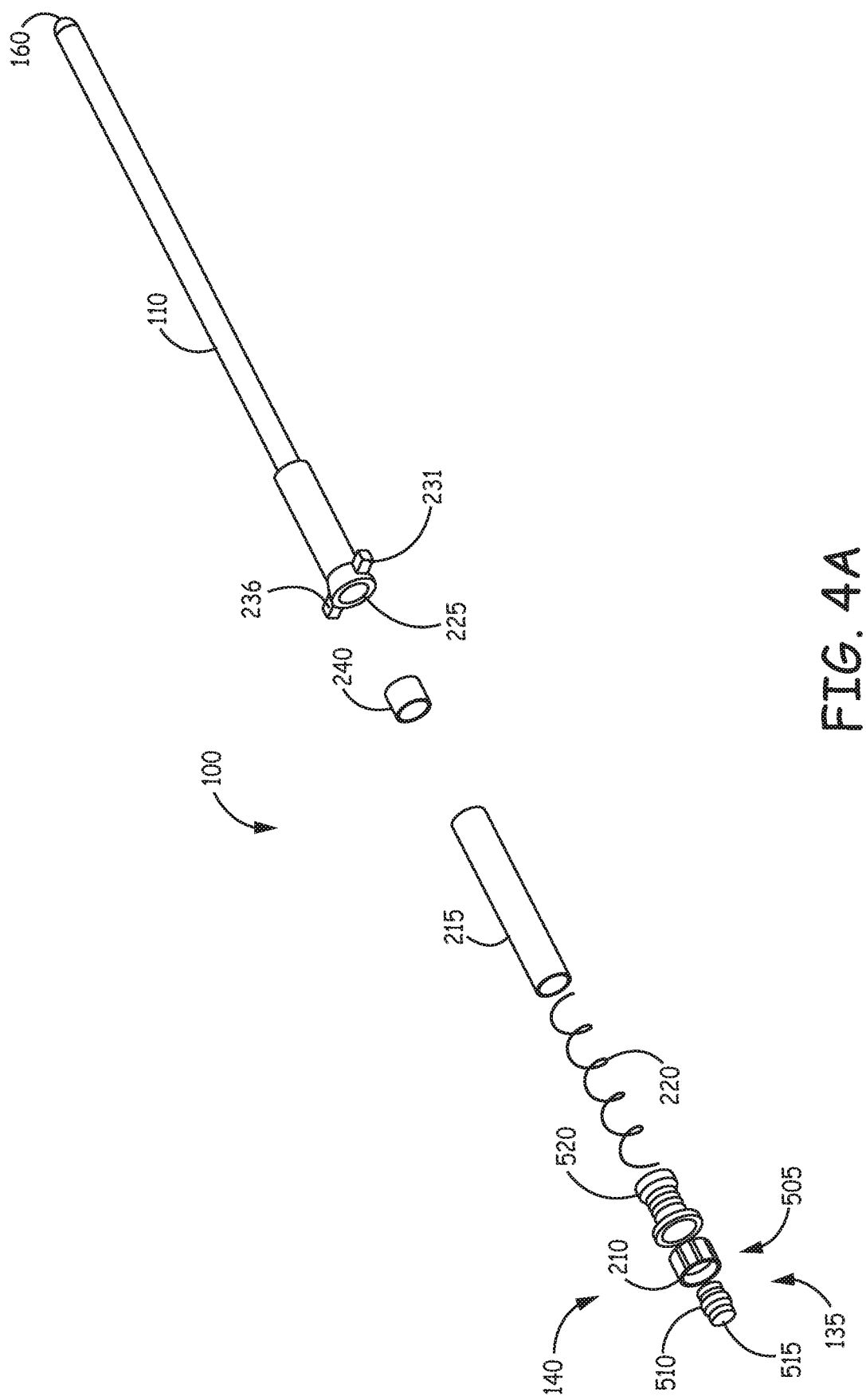
FIG. 4A is an exploded illustration of an example embodiment of a hemodialysis vascular access device.

FIG. 4A is an exploded illustration of an example embodiment of a hemodialysis vascular access device 100 showing the sleeve, components of the movable section 140, cuff 240, fixation structure 225 and other components described herein.

Figure 4B:
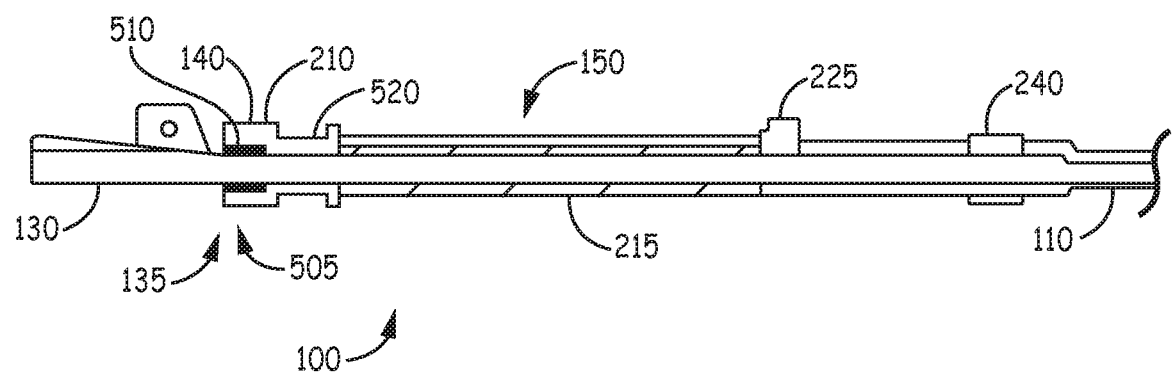
FIG. 4B is a longitudinal section view an example embodiment of a hemodialysis vascular access device with a catheter inserted in the device.

FIG. 4B is a cross-sectional view of an example vascular access device 100 and a catheter 130 inserted into the device. The catheter 130 can be secured to the vascular access device 100 using a cap assembly 505 (shown in detail in FIG. 5C) secure that compresses one or more seal members 510 against the catheter to form a fluid tight seal.

In some examples, the proximal end of the access device 100 is configured to sealably attach to a variety of hemodialysis catheters, i.e. the device can be compatible with different brands of catheters or families of catheters. In an example, the device 100 can be compatible with CVC catheters, Bard® HemoSplit™ long term hemodialysis catheters, as well as catheters available from Medtronic Covidien, such as the Palindrome™ family of catheters.

Figure 5B:
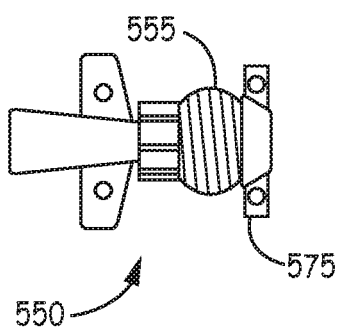

FIGS. 5A and 5B, are illustrations of a portion an example access device 550 with a compressible section 555 formed from a balloon. A tubular balloon structure 560 extends from a proximal end 555 of the device, around a shaft of a hemodialysis catheter 570, to a fixation structure 575. The balloon can be sized and shaped to permit inflation without stretching of the balloon material to avoid pressurizing the system. In some exemplary embodiments the balloon can contain a liquid fluid instead of gaseous fluid, provided with an optional external overflow. In some embodiments the fluid can contain anti-microbial and/or anti-bacterial agents.

The balloon 560 can be compliant, or non-compliant, and the balloon material may be elastic, or largely inelastic. In some examples, the balloon material can be latex, acrylonitrile, non-latex, polyurethane, Pebax, nylon or polyethylene terephthalate or a blend of the above.

As shown in FIG. 5B, when the proximal end 565 of the access device is moved toward the fixation structure 575, the balloon structure 560 expands. In this manner, the access device may provide a closed system and avoid the need for valves or permeable membranes. In some examples, a valve or permeable membrane is used in conjunction with the balloon as a supplemental or pressure relief valve. In some embodiments, an airtight seal can be provided where the catheter enters fixation structure 575. This would cause any pressurized air to remain in the balloon rather than migrating into the sleeve. In some examples, the seal could be configured as shown in FIGS. 6A-J.

Figure 5C:
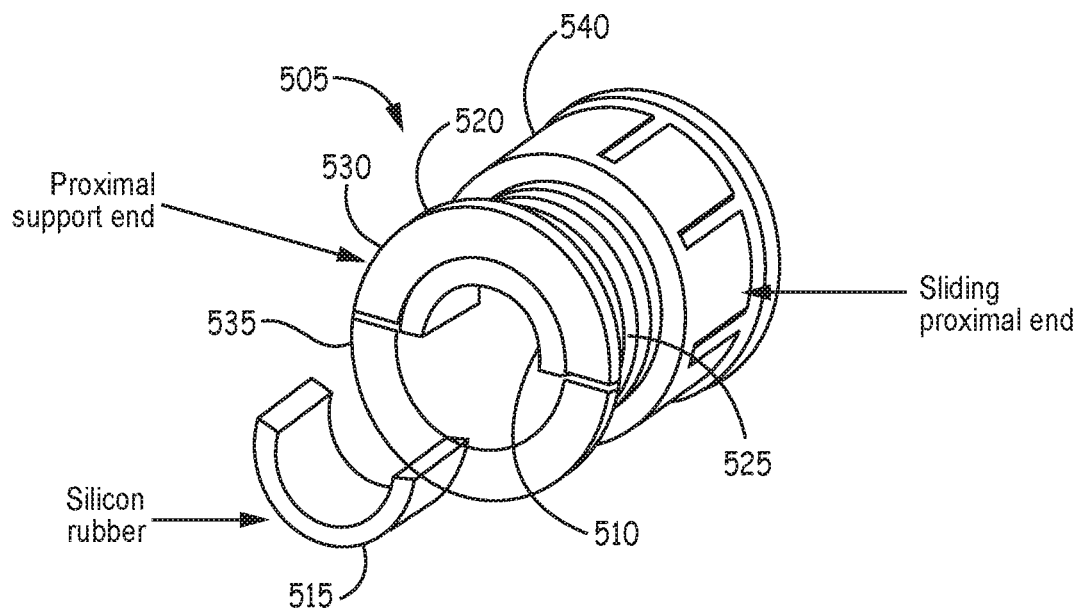
FIG. 5C is a perspective view of an example cap and seal for coupling an access device to a hemodialysis catheter.

FIG. 5C is a perspective view of an example cap and seal assembly 505 for coupling an access device to a hemodialysis catheter. In an example, compressible seal members 510, 515 reside inside a support structure 520, which may be a cylindrical tube sized and shaped to receive seal members 510, 515 inside the tube. Exemplary embodiments include compressible seal members 510 and 515 made such that receiving devices with oval or other form cross-sections can be tightly sealed in the cap and seal assembly.

Threads 525 may be provided on an outside surface of the support structure 520 to mate with internal threads on a rotating cap 540. In an example, the support structure can be formed with a gap 525 that allows for compression of an upper section 530 and against a lower section 535 by the cap, which compresses the seal members 510, 515 against a tube, e.g. a hemodialysis catheter shaft 130, that can be inserted through the assembly 505. Other embodiments include a gap with sufficient space to accept a cuff on the hemodialysis catheter to enter the sleeve.

In an example embodiment, this structure can be used as component of the access device 100 shown in FIGS. 1, 2A, 2B, 3A, and 3C. In some examples, an alternative structures can be used to seal the access device against the catheter. In some examples, a Tuohy Borst valve adapter structure can be used. Another example hemostasis sealing device is described in U.S. Publication number 20120221024 (Sutton et al.), which is incorporated by reference in its entirety.

In some examples, the valve at the distal end of the catheter can be a mechanical valve that has a neutral closed state, i.e. it closes itself, unless biased open. FIGS. 6A-F illustrate various valve configurations that block the flow of blood into a sleeve 600 but permit a catheter (not shown) to pass through the valve. The valve may be formed, for example, of CARBOTHANE™. Other flexible biocompatible materials may also be used, such as silicone, PU, bio-compatible rubbers (latex, non-latex). In some examples, a valve can include leaflets that flex to allow a catheter to pass through the valve. In some examples, the leaflets substantially seal against the catheter to partially or fully block the passage of blood into the catheter. In some examples, the leaflets return to a closed configuration when the catheter is withdrawn from the valve. In some examples, portions of the valve are covered with a coating, such as a low friction, friction reducing coating, lubricating materials (e.g. silicone oil) or a lubricious coating.

FIGS. 6A-6J show various examples of valve configurations at the distal end of the device. While for the purpose of illustration the valves are shown at the distal end of the device 100, as previously described, in some examples the valve configurations in FIGS. 6A-6J could be employed to seal around a catheter 130 at the proximal end of the device.

Figure 6A:
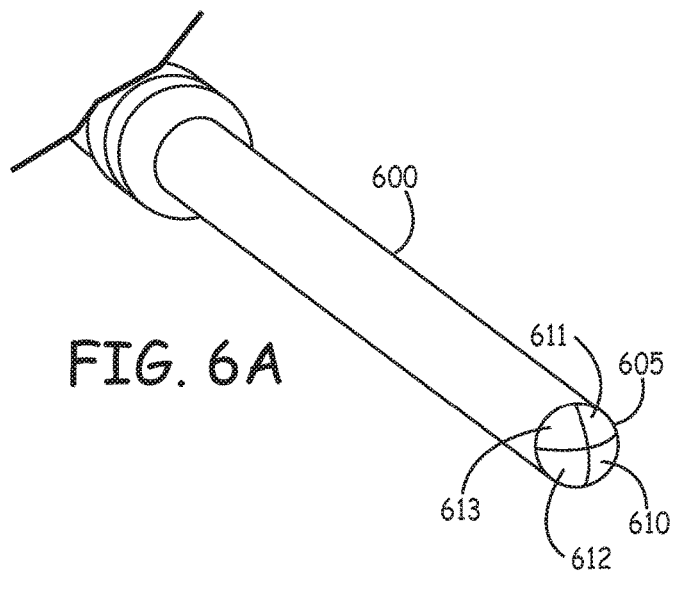
FIG. 6A is a perspective view of an example valve configuration at a distal end of the access device.

FIG. 6A is a perspective view of an example valve configuration with a plurality of leaflets situated at a distal end of the access device. The valve 605 has a plurality of leaflets 610, 611, 612, 613 which may be provided in a dome shape that may have a circumference that is approximately the same as the circumference of the sleeve. When a catheter is pressed against the leaflets 610, the leaflets flex distally to allow the catheter to pass through the valve 605.

Figure 6B:
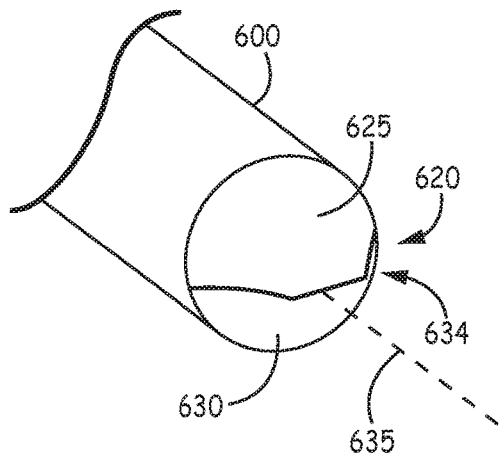
FIG. 6B is a perspective view of an example valve configuration at a distal end of the access device.
Figure 6C:
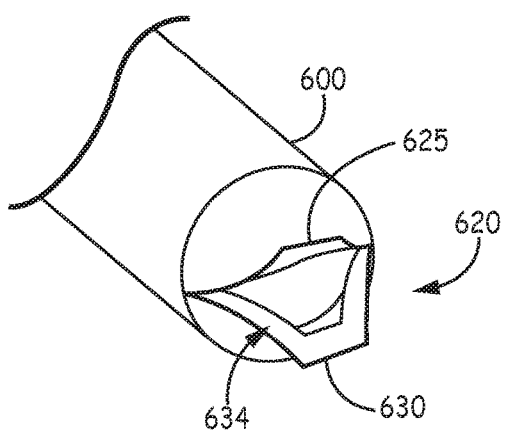
FIG. 6C is a perspective view of an example valve configuration at a distal end of the access device.

FIGS. 6B and 6C are perspective views of an example valve 620 configuration at a distal end of the access device. The valve 620 is provided in a split configuration, with a top portion 625 and bottom portion 630 extending distally from the sleeve 600 and converging to a narrowed mouth 634 at a distal end of the seal. As shown in FIG. 6C, the top portion 625 and bottom portion 630 can flex away from the central axis of the sleeve 635 to permit a catheter to pass through the valve. Thickness of material in distal portion of valve maybe thicker than thickness of material in proximal portion of valve. This may allow for firmer closing and a better seal.

Figure 6D:
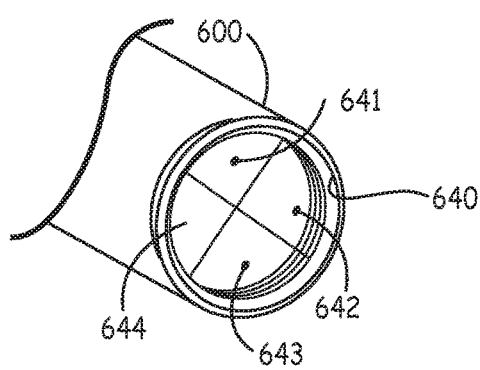
FIG. 6D is a perspective view of an example valve configuration at a distal end of the access device.

FIG. 6D is a perspective view of an example valve configuration at a distal end of the access device. A plurality of leaflets 641, 642, 643, 644 extend inwardly from an outer wall 640 of sleeve 600. The leaflets 641, 642, 643, 644 may be arranged in a plane that is substantially perpendicular to the longitudinal axis of the sleeve 600. The leaflets 641, 642, 643, 644 flex to allow a catheter to pass through the valve.

Figure 6E:
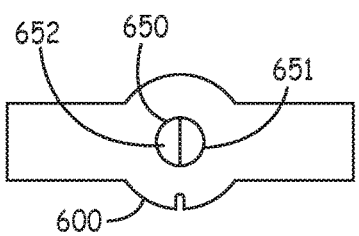
FIG. 6E is an end view of an example valve configuration at a distal end of the access device.
Figure 6F:
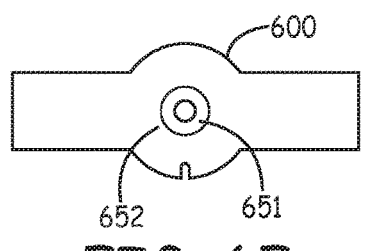
FIG. 6F is an end view of an example valve configuration at a distal end of the access device.

FIGS. 6E and 6F are end views of an example valve configuration at a distal end of the access device. The device has a valve section 650 with at least two leaflets 651, 652 extending into the interior of the sleeve. The leaflets 651, 652 connect to form a seal. When a catheter 655 is pushed through the valve, the leaflets 651, 652 deflect and deform to accommodate the catheter.

Figure 6G:
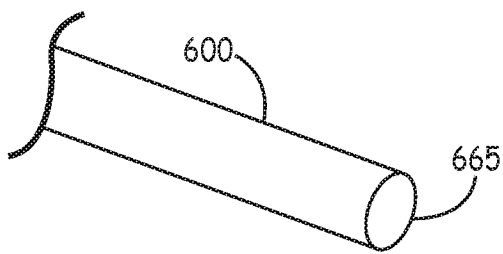
FIG. 6G is a perspective view of the distal end of an example access device with a balloon configured to close a distal orifice.
Figure 6H:
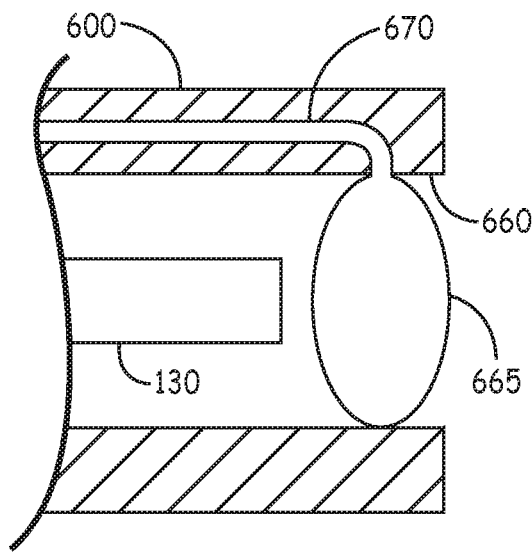
FIG. 6H is a cross sectional view of an example access device with a balloon configured to close a distal orifice.

FIGS. 6G and 6H are respectively perspective and sectional illustrations an example where an access device has a sleeve 600 with a distal tip orifice 660 that can be closed off with a small balloon 665 positioned at the orifice. When fluid is delivered through an inflation lumen 670 running through the sleeve to the balloon, the balloon 665 expands to seal the distal tip orifice 660. When the catheter 130 is moved distally in the sleeve, it pushes against the balloon and pivots, deflects, or deforms the balloon 665 to move out of the sleeve and into the blood.

Figure 6I:
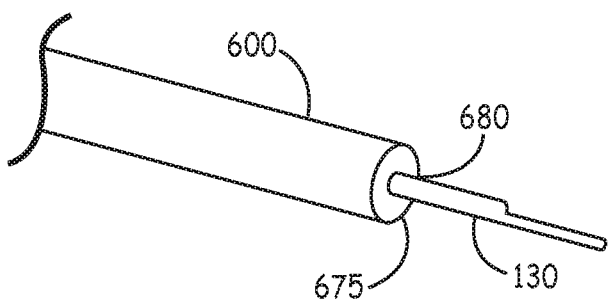
FIG. 6I is a perspective view of the distal end of an example access device with an annular balloon configured to close a distal orifice.
Figure 6J:
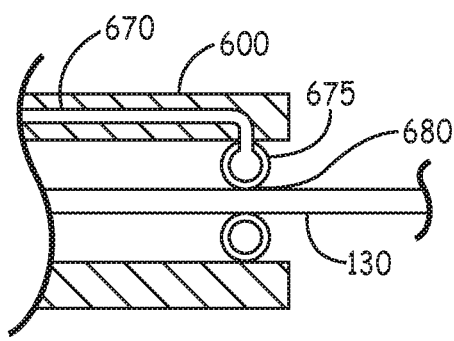
FIG. 6J is a cross sectional view of an example access device with an annular balloon configured to close a distal orifice.

FIGS. 6I and 6J are respective perspective and sectional illustrations of an example with an annular balloon 675. The balloon, when inflated, can seal the distal tip orifice 660. Catheter 130 can be inserted through orifice 680 in the annular balloon 675. The balloon 675 can seal around the catheter 130. In an example, the balloon 675 flexes or deforms to accommodate the catheter 130 through the orifice. In an example, the balloon 675 can be partially deflated accommodate passage of the catheter 130. In some examples, the balloon 675 can accommodate passage of the catheter when fully inflated.

Other configurations of an access device 100 are possible to enable movement of the moveable portion 140 with respect to the sleeve 110. The various examples shown in FIGS. 7A to 7E can be incorporated into an access device 100.

In some examples, in lieu of or in addition to a compressible section, the proximal portion of access device 100 includes a tube with at least two valves or seals. As shown in the example device 700 illustrated in FIG. 7A, a proximal portion of a vascular access device 700 includes a tube 705, a proximal sealing valve 710, and a distal sealing valve 715 spaced from the proximal sealing valve 710. The sealing valves 710, 715, can be configured, for example, similar to the distal valve examples shown in FIGS. 6A-6E, or as variations of compressible seals as illustrated in FIG. 5C. Other seal configurations, such as appropriately sized ring seals can also be used. The seals prevent contaminants such as bacteria or particles from entering the tube. In an example, the distance between the proximal seal and distal seal is larger than the expected or maximum amount of distal movement of the catheter within the sleeve, such that a sterilized portion of the catheter 130 may remain in either the tube 705 or sleeve and is not exposed to contaminants outside the body. In some examples, the catheter 130 can be held in place by friction between uses by one or both of the valves 710, 715.

Figure 7A:
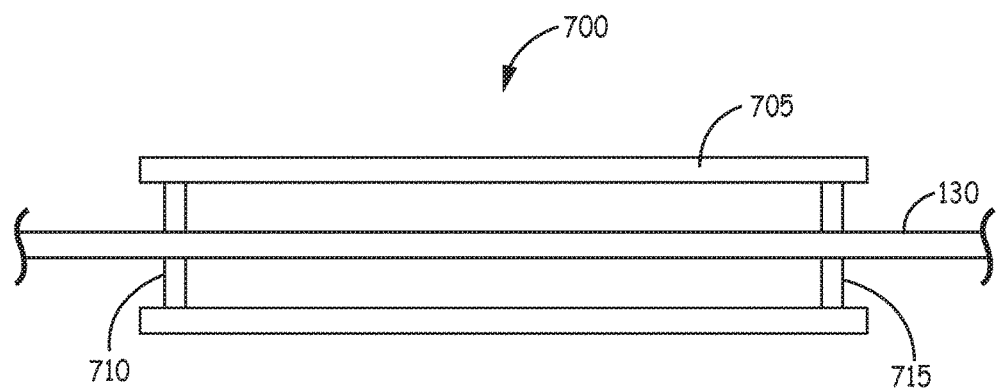
FIGS. 7A-7E are cross-sectional views of various example tube assemblies of an example access devices.
Figure 7B:
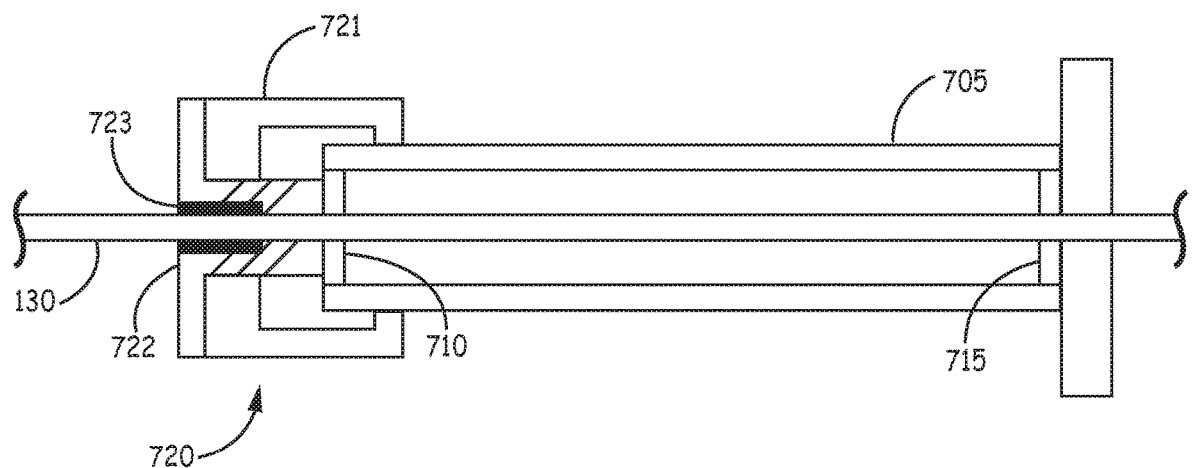

As shown in FIG. 7B, in some examples the catheter can be held in place by a releasable locking assembly 720, which in an example can be configured similar to the assembly 505 shown in FIG. 5. Cap 721 can be advanced on threads on compression piece 722 to compress a seal 723 against the catheter 130.

In some examples, a vascular access device can include a tube assembly with a moveable component sealably and slidably disposed inside a tube can allow for axial movement of the catheter with respect to the sleeve. In various examples, the moveable component can be disc, a cylinder or other solid form, or an inner tube. The moveable component can include an orifice that accommodates a catheter extending through the moveable component, so that the moveable and catheter move together in the tube assembly. In some examples, the moveable component incorporates a seal, such as one of the seals shown in FIG. 6A-6E valve, or a compressible seal that can be compressed using a rotary component, to seal the moveable component against the outer surface of the catheter. A valve may be provided in the seal assembly to allow passage of air, but not particles, into and out of a chamber formed by the moveable component and the outer tube.

Figure 7C:
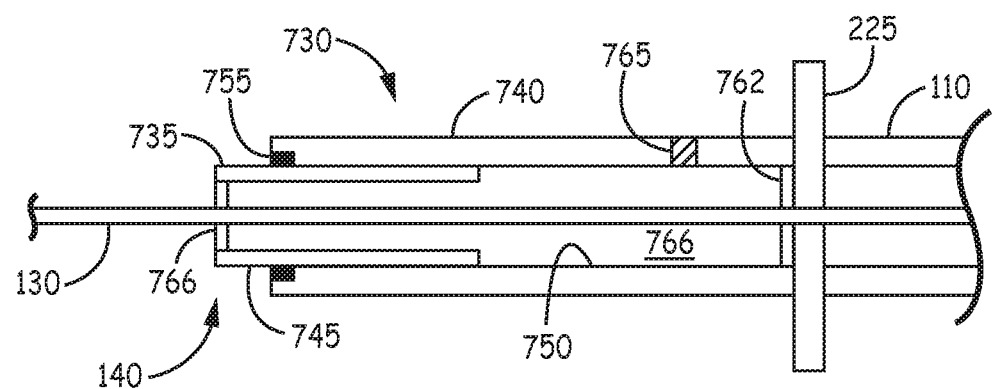
Figure 7D:
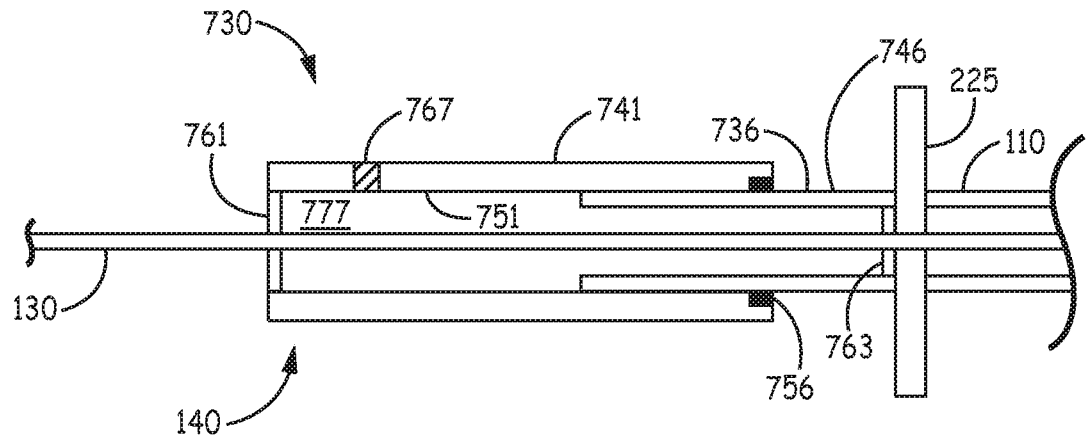

Referring now to FIGS. 7C and 7D, in some examples, a tube assembly 730 enables movement of the moveable portion 140 with respect to the sleeve 110. In the example shown in FIG. 7C, a moveable inner tube 735 is slidably inserted inside of an outer tube 740 to form tube assembly 745 that is coupled to the sleeve 110.

In the example shown in FIG. 7D, a moveable outer tube 736 slides over an inner tube 741. The inner tube 735, 736 has an outer shape and dimension that substantially matches in an inner diameter of the outer tube 740, 741. The inner and outer tube may have cross-sections (not shown) that are circular, elliptical, ovular, or other shapes. In some examples, a seal 755, 756 extends around an outside surface 745, 746 of the inner tube 735, 736 to seal the inner tube against an inner surface 750, 751 of the outer tube 740, 741. A seal 760, such as a ring seal or a seal as shown in FIGS. 6A-J, can seal against the outer surface of catheter 130. A distal seal 762, 763 can be provided at a distal end of the tube assembly and can seal against the catheter 130. In some examples, a valve 765 is provided in or on the outer tube 740, 741 or inner tube 735, 736 to allow air to move into or out of a chamber 766, 777 created by the tubes. In the examples shown in FIGS. 7C and 7D, the tube assembly 730 may be integral with the fixation structure 225, or coupled to the fixation structure. In some examples, a tube assembly 730 can be coupled to a catheter 130 so that the moveable portion 130 moves with the catheter. For example, a cap and seal assembly (not shown in FIG. 7C or 7D), such as the assembly 505 illustrated in FIG. 5C, can be coupled to the inner tube 735 in FIG. 7C or outer tube 741 shown in FIG. 7D to provide connection to a catheter 130.

Referring now to FIG. 7C, as the inner tube 735 is displaced into the outer tube 740, the catheter 130 moves distally into the sleeve, and, if a valve 765 is provided, air moves through the valve out of the chamber 766. When the inner tube 735 is pulled backward out of the outer tube 740, the catheter 130 retracts, and if a valve 765 is provided, air moves through the valve into the chamber.

Referring now to FIG. 7D, as the outer tube is moved distally toward the inner tube, the catheter protrudes from the sleeve 110, and air moves out of the chamber 777 through valve 767.

Figure 7E:
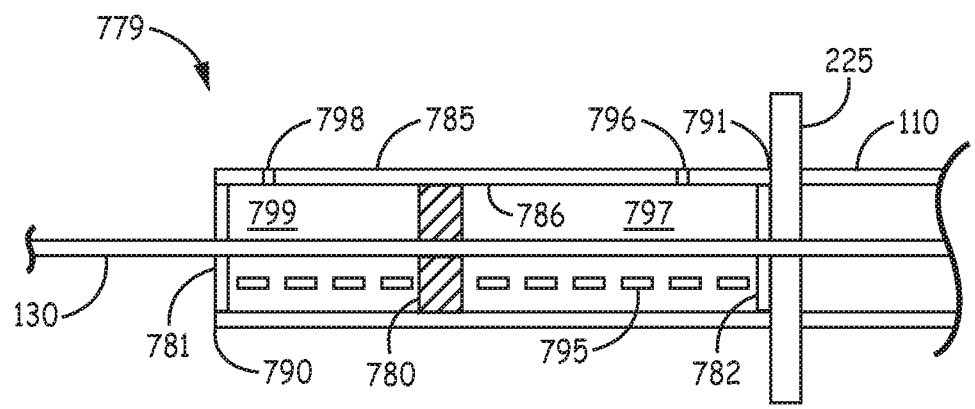

As shown in FIG. 7E, in an example vascular access device, a tube assembly 779 slidable component 780 is attached to the catheter 130 and captured in a tube 785. The slidable component 780 may seal against the inner surface 786 of the tube 785, or a ring seal (not shown) may be provided to create a seal between the slidable component 780 and the tube 785. The tube may have a seal 781 on the proximal end 790. A distal seal 782 may also be provided on the distal end 791 of the tube 785. The tube 785 can be integral with our coupled to a fixation component 225 that is fixable to a human body. In an example, the movable component 780 is releasably attachable to a catheter 130, e.g. using a compressible seal, or an assembly configured similar to the assembly shown in FIG. 5C. The tube 785 can include a longitudinal hinge 795 and a longitudinal seal (not shown) so that the tube 785 can be opened to receive the catheter and moveable component 780 and subsequently closed and sealed. In an example, when the catheter 130 is moved distally to extend the distal end of the catheter out of the sleeve 110 and into blood, the movable component 780 moves distally with the catheter inside the tube 785. The tube assembly can include a distal valve 796 that releases air from a chamber 797 when the slidable component 780 is moved distally and allows air into the chamber 797 when the slidable component is moved proximally. The tube assembly can also include a proximal valve 798 to release air from proximal chamber 799 when the component 780 is moved proximally in the tube, and allow air into the proximal chamber proximal when the component 780 is moved distally.

Figure 8:
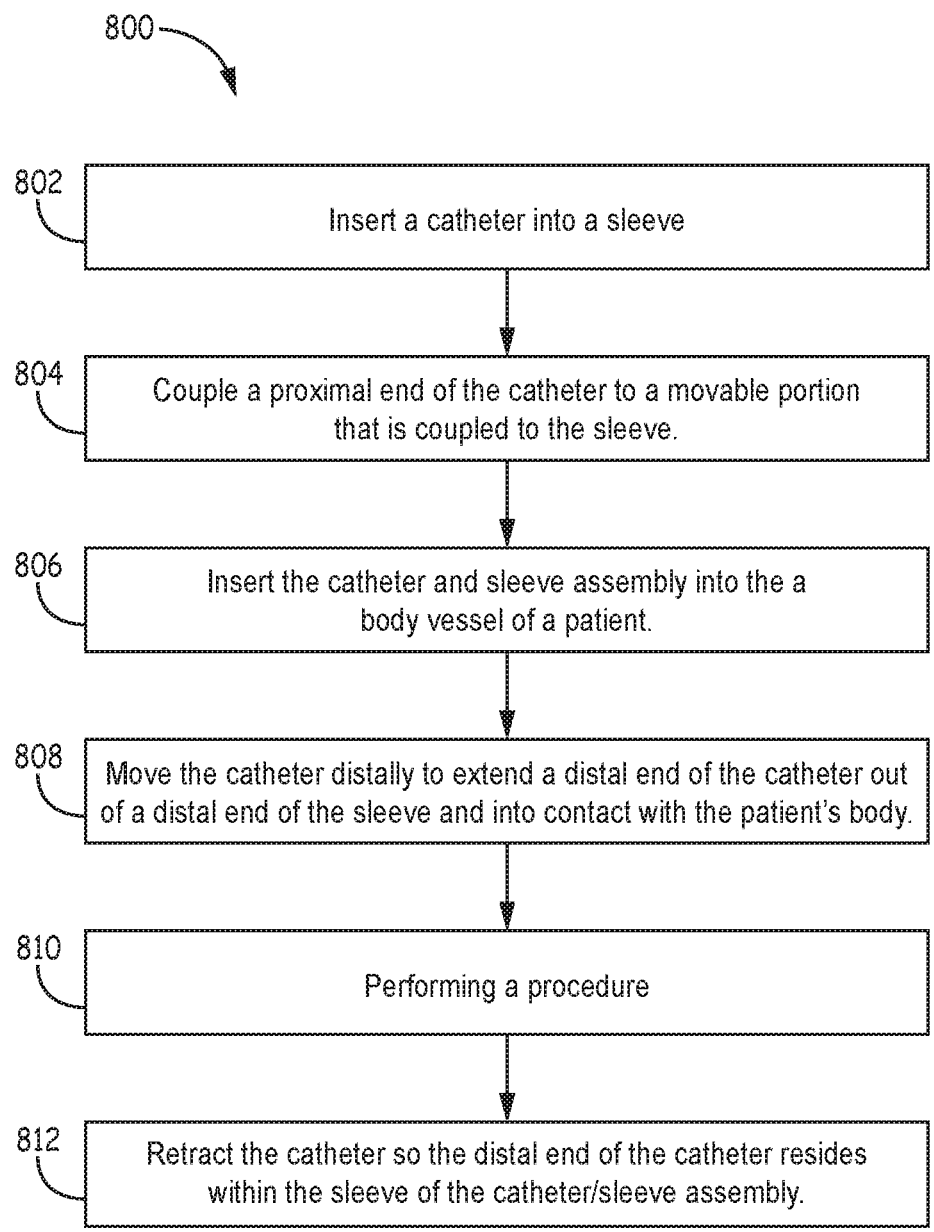
FIG. 8 is a flowchart that illustrates an example method of using an access device in a medical procedure such as a hemodialysis procedure.

FIG. 8 is a flowchart that illustrates an example method 800 of using an access device in a medical procedure. At 802, a catheter is inserted into a sleeve, such as a sleeve of the various examples of a vascular access device 100 described herein. At 804, a proximal end of the catheter is coupled to a movable portion that is coupled to the sleeve to form a catheter/sleeve assembly. In an example, the proximal end of the catheter is coupled to a compressible section, such as a section as shown in FIGS. 1, 2A, 2B, 3A, and 3B. In an example, the catheter can be positioned in the sleeve with a desired length protruding from distal end of sleeve when the compressible portion is in a compressed configuration, and a location is marked, or positioned secured. In an example, a movable portion of an access device is actuated, e.g. by compressing a compressible region or sliding a component in a tube, to project a distal end of the catheter out of the sleeve, so that a desired catheter protrusion length can be obtained. In an example, the catheter is a hemodialysis catheter.

At 806, the catheter and sleeve assembly is inserted into a body vessel of a patient, such as a blood vessel. At 808, the catheter is moved distally to extend a distal end of the catheter out of a distal end of the sleeve and into contact with the patient's body. In an example, the catheter is moved into a blood vessel so that it in in the patient's blood. When the medical procedure is a dialysis procedure, at 810, dialysis of the patient's blood is provided by withdrawing blood through the catheter, treating the blood, and returning the blood to the body through the catheter. At 812, the catheter is retracted, so that the distal end of the catheter resides within the sleeve of the catheter/sleeve assembly.

In some examples, various access device configurations may be provided with sleeves in various lengths to accommodate various catheter lengths. In some examples, the length of the sleeve can be variable, through adjustment of parts, or through selection of components of particular lengths. In some examples, access devices can be provided with a variety of stroke lengths, i.e. the length over which the movable section can move, and thus the distance that the distal end of the hemodialysis catheter can move, can be varied to suit a particular application. In some applications, the stroke length of an access device can be variable, for example by adjustment of mechanical stops.

In some examples, a hemodialysis catheter can be removable and replaceable, in the event that an original catheter becomes obstructed or otherwise compromised. Hemodialysis catheters are shown for example in U.S. Pat. Nos. 6,156,016 and 6,190,371, which are incorporated by reference.

While various examples are described in the context of a hemodialysis application, an access device could be used with an indwelling catheter in other scenarios, such as central venous access for numerous reasons including: chemotherapy, parenteral nutrition, saline and fluid delivery, drug delivery, antibiotic delivery, frequent blood draws, blood stem cell collection, plasmapheresis, and monitoring of central venous pressure. Venous access can be either through tunneled or non-tunneled catheters and can be directly into central veins such as the subclavian or jugular veins or inserted into peripheral veins using a longer catheter to provide central access called a peripherally inserted central catheter (PICC) line.

In some examples, portions of the access device 100, catheter 130, or both may be covered with a coating. For example, hydrophilic polymeric base coatings can be applied to portions of the medical device to impart lubricity and decrease particulate shedding. In some examples, portions of the valve on the distal end of the sleeve are covered with a coating. In other examples, the inner diameter of the sleeve is coated or lined with lubricious low friction coatings or the outer diameter is lined with lubricious low friction coatings, friction reducing or lubricating materials such as silicone oil, perfluorinated oils or waxes or with covalently bonded coating that imparts lower friction.

Low Friction Surfaces

Exemplary embodiments of low friction surfaces for the vascular access devices described herein include substrates prepared from low friction materials (e.g. PTFE and PTFE liners) and surfaces that can be made to be low friction by addition of coatings (e.g. coatings with hydrophilic polymers).

One class of hydrophilic polymers useful as polymeric materials for hydrophilic base coat formation can be synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly (HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,Ndimethylacrylamide-co-aminopropylmethacrylamide) and poly(acrylamide-co-N,Ndimethylaminopropylmethacrylamide) are described in example 2 of U.S. Pat. No. 7,807,750 (Taton et al.), the disclosure of which is incorporated herein by reference.

Other hydrophilic polymers that can be useful in the present disclosure are derivatives of acrylamide polymers with photoreactive groups. One such representative hydrophilic polymer can be the copolymerization of N-[3-(4-benzoylbenzamido)propyl]methacrylamide (Formula I) with N-(3-aminopropyl)methacrylamide (Formula II) to produce the polymer poly(N-3-aminopropyl)methacrylamide-co-N-[3-(4-benzoylbenzamido)propyl]methacrylamide (Formula III). The preparation of the polymer is disclosed in Example 1 of US Patent Publication 2007/0032882 (to Lodhi, et al.), the full content of which is incorporated herein by reference.

Formula I

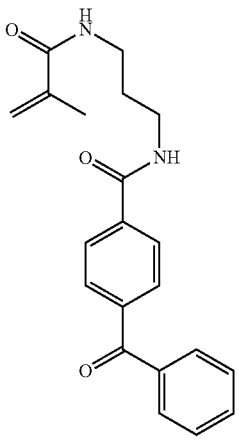

Formula II

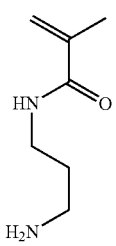

Formula III

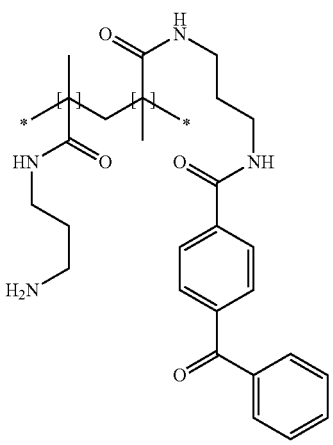

In some embodiments, the hydrophilic polymer can be a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Pat. No. 7,807,750 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. Aryl ketones herein can specifically include diaryl ketones. Polymers herein can provide a hydrophilic polymer having a pendent activatable photogroup that can be applied to the expandable and collapsible structure, and can then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Hydrophilic photo-polyacrylamide polymers such as poly(acrylamide-co-N-(3-(4-benzoylbenzamido)propyl)methacylamide), "Photo PA", and derivatives thereof can be used to form hydrophilic base coats in exemplary embodiments of the present disclosure. Methods for the preparation of photo-polyacrylamide are described in U.S. Pat. No. 6,007,833, the disclosure of which is incorporated herein by reference.

Other embodiments of hydrophilic base coats include derivatives of photo-polyacrylamide polymers incorporating additional reactive moieties. Some exemplary reactive moieties include N-oxysuccinimide and glycidyl methacrylate. Representative photo-polyacrylamide derivatives incorporating additional reactive moieties include poly(acrylamide-co-maleic-6-aminocaproic acid-N-oxysuccinimide-co-N-(3-(4-benzoylbenzamido)propyl)methacrylamide) and poly(acrylamide-co-(3-(4-benzoylbenzamido)propyl)methacrylamide)-co-glycidylmethacrylate. Additional photo-polyacrylamide polymers incorporating reactive moieties are described in U.S. Pat. No. 6,465,178 (to Chappa, et al.), U.S. Pat. No. 6,762,019 (to Swan, et al.) and U.S. Pat. No. 7,309,593 (to Ofstead, et al.), the disclosures of which are herein incorporated by reference.

Other embodiments of exemplary hydrophilic base coats that include derivatives of photo-polyacrylamide polymers incorporating additional reactive moieties can be found in U.S. Pat. No. 6,514,734 (to Clapper, et al.), the disclosure of which is incorporated herein by reference in its entirety.

In yet other embodiments, the hydrophilic base coat can include derivatives of photo-polyacrylamide polymers incorporating charged moieties. Charged moieties include both positively and negatively charged species. Exemplary charged species include, but are not limited to, sulfonates, phosphates and quaternary amine derivatives. Some examples include the negatively charged species N-acetylated poly(acrylamide-co-sodium-2-acrylamido-2-methylpropanesulfonate-co-N-(3-(4-benzoylbenzamido)propyl)methacrylamide)-co-methoxy poly(ethylene glycol) monomethacrylate. Other negatively charged species that can be incorporated into the hydrophilic base coat are described in U.S. Pat. No. 4,973,993, the disclosure of which is incorporated herein by reference in its entirety. Positively charged species can include poly(acrylamide-co-N-(3-(4-benzoylbenzamido)propyl)methacrylamide)-co-(3-(methacryloylamino)propyl)trimethylammonium chloride. Other positively charged species that can be incorporated into the hydrophilic base coat are described in U.S. Pat. No. 5,858,653 (to Duran et al.), the disclosure of which is incorporated herein by reference in its entirety.

In another embodiment, the polymers and copolymers as described are derivatized with one or more polymerizable group(s). Polymers with pendent polymerizable groups are commonly referred to as macromers. The polymerizable group(s) can be present at the terminal portions (ends) of the polymeric strand or can be present along the length of the polymer. In one embodiment polymerizable groups are located randomly along the length of the polymer.

Exemplary hydrophilic polymer coatings can be prepared using polymer grafting techniques. Polymer grafting techniques can include applying a nonpolymeric grafting agent and monomers to a substrate surface then causing polymerization of the monomers on the substrate surface upon appropriate activation (for example, but not limited to, UV radiation) of the grafting agent. Grafting methods producing hydrophilic polymeric surfaces are exemplified in U.S. Pat. Nos. 7,348,055; 7,736,689 and 8,039,524 (all to Chappa et al.) the full disclosures of which are incorporated herein by reference.

Optionally, the coating can include a crosslinking agent. A crosslinking agent can promote the association of polymers in the coating, or the bonding of polymers to the coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photo-crosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenylmethyleneoxy) benzene-1, 3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis [2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603, 040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivable crosslinking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional crosslinking agents can include those having formula Photo1-LG-Photo2, wherein Photo1 and Photo2 independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

Crosslinking agents used in accordance with embodiments herein can include those with at least two photoreactive groups. Exemplary crosslinking agents are described in U.S. Pat. No. 8,889,760, the content of which is herein incorporated by reference in its entirety.

In some embodiments, the first and/or second crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, at least one of the first and second crosslinking agents comprising a linking agent having formula Photo1-LG-Photo2, wherein Photo1 and Photo2, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and second crosslinking agents comprising a linking agent having a formula selected from:

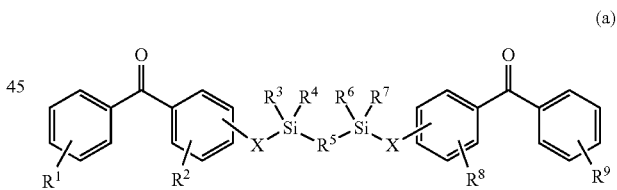

(a)

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

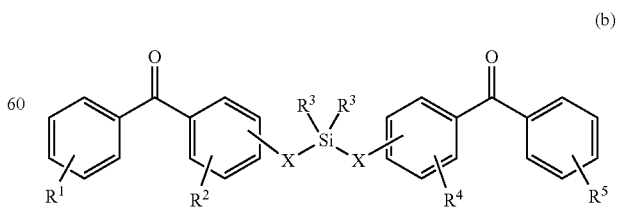

(b)

wherein R1 and R5 are any substitution; R2 and R4 can be any substitution, except OH; R3 can be alkyl, aryl, or a combination thereof; and X, independently, are O, N, Se, S, alkylene, or a combination thereof;

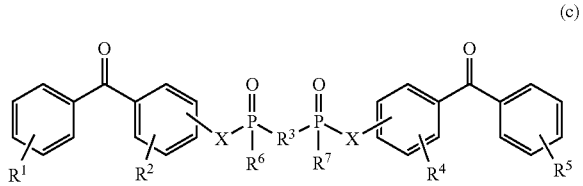

wherein R1, R2, R4 and R5 are any substitution; R3 is any substitution; R6 and R7 are alkyl, aryl, or a combination thereof; and each X can independently be O, N, Se, S, alkylene, or a combination thereof; and

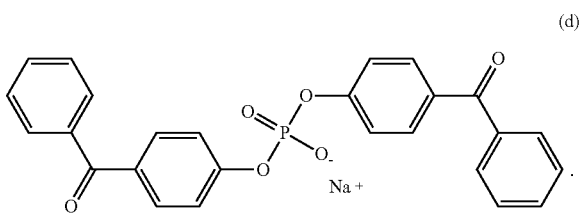

In a particular embodiment, the crosslinking agent can be bis(4-benzoylphenyl) phosphate.

In some embodiments, the photoactivatable crosslinking agent can be ionic, and can have good solubility in an aqueous composition, such as the first and/or second coating composition. Thus, in some embodiments, at least one ionic photoactivatable crosslinking agent is used to form the coating. In some cases, an ionic photoactivatable crosslinking agent can crosslink the polymers within the second coating layer which can also improve the durability of the coating.

Any suitable ionic photoactivatable crosslinking agent can be used. In some embodiments, the ionic photoactivatable crosslinking agent is a compound of formula I: X1-Y—X2 where Y is a radical containing at least one acidic group, basic group, or a salt of an acidic group or basic group. X1 and X2 are each independently a radical containing a latent photoreactive group. The photoreactive groups can be the same as those described herein. Spacers can also be part of X1 or X2 along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; X1 and X2 can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; X1 and X2 can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis(4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable crosslinking agent can be a compound having the formula:

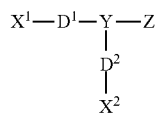

wherein X1 includes a first photoreactive group; X2 includes a second photoreactive group; Y includes a core molecule; Z includes at least one charged group; D1 includes a first degradable linker; and D2 includes a second degradable linker. Additional exemplary degradable ionic photoactivatable crosslinking agents are described in US Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula XR1R2R3R4, where X is a chemical backbone, and R1, R2, R3, and R4 are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

PG2-LE2-X-LE1-PG1 wherein PG1 and PG2 include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; LE1 and LE2 are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Further embodiments of non-ionic photoactivatable crosslinking agents can include, for example, those described in U.S. Pat. Publication 2013/0143056 (Swan et al., "Photo-Vinyl Primers/Crosslinkers"), the disclosure of which is incorporated herein by reference. Exemplary crosslinking agents can include non-ionic photoactivatable crosslinking agents having the general formula R1-X—R2, wherein R1 is a radical comprising a vinyl group, X is a radical comprising from about one to about twenty carbon atoms, and R2 is a radical comprising a photoreactive group.

A single photoactivatable crosslinking agent or any combination of photoactivatable crosslinking agents can be used in forming the coating. In some embodiments, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis(4-benzoylbenzyldimethylammonium) salt or at least one anionic photoactivatable crosslinking agent such as 4,5-bis(4-benzoyl-phenylmethyleneoxy)benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Publ. Pat. App. No. 2010/0274012 (to Guire et al.) and U.S. Pat. No. 7,772,393 (to Guire et al.) the content of all of which is herein incorporated by reference.

In some embodiments, crosslinking agents can include boron-containing linking agents including, but not limited to, the boron-containing linking agents disclosed in US Pat. Publication 2013/0302529 entitled "Boron-Containing Linking Agents" by Kurdyumov et al., the content of which is herein incorporated by reference. By way of example, linking agents can include borate, borazine, or boronate groups and coatings and devices that incorporate such linking agents, along with related methods. In an embodiment, the linking agent includes a compound having the structure (I):

wherein R1 is a radical comprising a photoreactive group; R2 is selected from OH and a radical comprising a photoreactive group, an alkyl group and an aryl group; and R3 is selected from OH and a radical comprising a photoreactive group. In some embodiments the bonds B—R1, B—R2 and B—R3 can be chosen independently to be interrupted by a heteroatom, such as 0, N, S, or mixtures thereof.

Additional agents for use with embodiments herein can include stilbene-based reactive compounds including, but not limited to, those disclosed in U.S. Pat. No. 8,487,137, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

Natural polymers can also be used to form the hydrophilic base coat. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In some instances a tie layer can be used to form the hydrophilic base layer. In yet other instances the tie layer can be added to the hydrophilic base layer. The tie layer can act to increase the adhesion of the hydrophilic base layer to the substrate. In other embodiments, the tie layer can act to increase adhesion of the hydrophobic active agent to the hydrophilic base layer. Exemplary ties layers include, but are not limited to silane, butadiene, polyurethane and parylene. Silane tie layers are described in US Patent Publication 2012/0148852 (to Jelle, et al.), the content of which is herein incorporated by reference.

In exemplary embodiments, the hydrophilic base layer can include tannic acid, polydopamine or other catechol containing materials.

The above detailed description is intended to be illustrative, and not restrictive. The scope of the disclosure should, therefore, be determined with references to the appended claims, along with the full scope of equivalents to which such claims are entitled.

What is claimed is:

1. A vascular access device comprising:
   a proximal orifice;
   a distal orifice; and
   an elongated catheter body defining
      a proximal portion defining a proximal end and a proximal lumen in communication with the proximal orifice;
      a distal portion defining a distal end and a distal lumen in communication with the distal orifice;
   the proximal lumen and distal lumen configured to receive a catheter through the proximal orifice and extending at least partially through the proximal lumen and distal lumen;
   the proximal end configured to be connected to the catheter;
   the proximal portion comprising a compressible section to allow the proximal orifice to be axially displaceable toward the distal portion from a first position to a second position, causing a distal end of the catheter to extend beyond the distal orifice when the proximal orifice is in the second position; and
   wherein the compressible section includes a balloon sized and shaped to at least partially inflate when the proximal orifice is displaced toward the distal portion.

2. The vascular access device of claim 1, the compressible section comprising an air permeable membrane.

3. The vascular access device of claim 2, wherein the air permeable membrane permits air movement out of the device as the proximal orifice moves from the first position to the second position.

4. The vascular access device of claim 2, wherein the air permeable membrane permits air movement into the device as the proximal orifice moves from the second position to the first position.

5. The vascular access device of claim 1, the compressible section comprising an antimicrobial membrane.

6. The vascular access device of claim 1, the compressible section comprising a protective cover.

7. The vascular access device of claim 6, the protective cover configured to be removed to allow the proximal orifice to move from the first position to the second position.

8. The vascular access device of claim 1, the compressible section comprising a spring.

9. The vascular access device of claim 1, the compressible section comprising a pleated material.

10. The vascular access device of claim 1, further comprising a valve proximate the distal orifice, the valve configured to allow passage of the catheter through the valve such that the catheter may extend through the valve and out of the distal orifice, the valve further configured to prevent the flow of blood into the distal lumen when the catheter is not extended through the valve.

11. The vascular access device of claim 10, the valve proximate the distal orifice comprising a plurality of leaflets.

12. The vascular access device of claim 10, the valve comprising a dome shape.

13. The vascular access device of claim 10, the valve covered with a coating comprising a lubricious coating.

14. The vascular access device of claim 1, further comprising a cap, the proximal end configured to be connected to the catheter via the cap.

15. A vascular access device comprising:
   a proximal orifice;
   a distal orifice; and
   an elongated catheter body defining
      a proximal portion defining a proximal end and a proximal lumen in communication with the proximal orifice;
      a distal portion defining a distal end and a distal lumen in communication with the distal orifice;
   the proximal lumen and distal lumen configured to receive a catheter through the proximal orifice and extending at least partially through the proximal lumen and distal lumen;
   the proximal end configured to be connected to the catheter;
   the proximal portion comprising a compressible section to allow the proximal orifice to be axially displaceable toward the distal portion from a first position to a second position, causing a distal end of the catheter to extend beyond the distal orifice when the proximal orifice is in the second position; and
   wherein the compressible section further comprises a tube assembly comprising a tube and a moveable component disposed inside the tube to allow the proximal orifice to move from the first position to the second position.

16. The vascular access device of claim 15, wherein the moveable component slides with respect to the tube.

17. The vascular access device of claim 1, further comprising a surface comprising polytetrafluoroethylene (PTFE) or PTFE liners.

18. The vascular access device of claim 1, further comprising a hydrophilic coated surface.

19. The vascular access device of claim 1, wherein the catheter is a dialysis catheter.

* * * * *